United States Patent
Lund et al.

(10) Patent No.: US 7,631,560 B2
(45) Date of Patent: Dec. 15, 2009

(54) METHODS OF INSPECTING ROTARY DRILL BITS

(75) Inventors: Jeffrey B. Lund, Cottonwood Heights, UT (US); Nicholas J. Lyons, Houston, TX (US); Eric C. Sullivan, Houston, TX (US); Terry D. Watts, Spring, TX (US)

(73) Assignee: Baker Hughes Incorporated, Houston, TX (US)

( * ) Notice: Subject to any disclaimer, the term of this patent is extended or adjusted under 35 U.S.C. 154(b) by 77 days.

(21) Appl. No.: 11/787,693

(22) Filed: Apr. 17, 2007

(65) Prior Publication Data

US 2007/0256862 A1 Nov. 8, 2007

Related U.S. Application Data

(60) Provisional application No. 60/792,445, filed on Apr. 17, 2006.

(51) Int. Cl.
*G01N 29/06* (2006.01)
*G01N 29/265* (2006.01)

(52) U.S. Cl. .............................. 73/629; 73/637; 73/606

(58) Field of Classification Search .................. 73/600, 73/622, 623, 624, 625, 627, 629, 632, 606, 73/634, 637, 638
See application file for complete search history.

(56) References Cited

U.S. PATENT DOCUMENTS

| | | | | |
|---|---|---|---|---|
| 2,971,372 | A | * | 2/1961 | Lewis et. al. .................. 73/600 |
| 4,020,688 | A | | 5/1977 | Hauldren |
| 4,041,773 | A | | 8/1977 | Hauldren et al. |
| 4,106,347 | A | | 8/1978 | DeKerlegand |
| 4,173,139 | A | | 11/1979 | Conn |
| 4,287,769 | A | | 9/1981 | Buckley |
| 4,361,044 | A | * | 11/1982 | Kupperman et al. .......... 73/623 |
| 4,379,408 | A | * | 4/1983 | Sandhu ........................ 73/603 |

(Continued)

FOREIGN PATENT DOCUMENTS

AU 563803 B2 7/1987

(Continued)

OTHER PUBLICATIONS

Anderson, T.L., Fracture Mechanics, $2^{nd}$ Edition, Chapters 2 and 9, 1995 by CRC Press, Inc.

(Continued)

*Primary Examiner*—John Fitzgerald
(74) *Attorney, Agent, or Firm*—TraskBritt

(57) ABSTRACT

A method for conducting nondestructive internal inspection of a rotary drill bit used for drilling subterranean formations comprises communicating ultrasonic waves into a drill bit and detecting ultrasonic waves that are reflected by at least a portion of the drill bit. In some embodiments, the waves may be directed into the drill bit from within a longitudinal bore thereof. Reflected waves also may be detected from within the bore. The methods may be used to develop threshold acceptance criteria for classifying drill bits as acceptable or unacceptable to prevent catastrophic failures of drill bits during use. Systems and apparatuses are disclosed for conducting nondestructive ultrasonic inspection of a drill bit used for drilling subterranean formations. The systems and apparatuses may comprise an ultrasonic probe configured for insertion within an internal longitudinal bore of a drill bit. Drill bits are disclosed that are configured to facilitate nondestructive ultrasonic inspection thereof.

14 Claims, 6 Drawing Sheets

U.S. PATENT DOCUMENTS

| | | | |
|---|---|---|---|
| 4,843,884 A * | 7/1989 | House et al. | 73/622 |
| 5,313,950 A | 5/1994 | Ishikawa et al. | |
| 5,373,907 A | 12/1994 | Weaver | |
| 5,813,480 A | 9/1998 | Zaleski, Jr. et al. | |
| 6,655,481 B2 | 12/2003 | Findley et al. | |
| 2002/0194916 A1* | 12/2002 | Yamada et al. | 73/627 |
| 2007/0102198 A1 | 5/2007 | Oxford et al. | |
| 2007/0102199 A1 | 5/2007 | Smith et al. | |
| 2007/0289385 A1* | 12/2007 | Kiuchi | 73/627 |

FOREIGN PATENT DOCUMENTS

| | | |
|---|---|---|
| WO | 0238916 A2 | 5/2002 |
| WO | 2006030787 A1 | 3/2006 |

OTHER PUBLICATIONS

PCT International Search Report for PCT/US2007/009305, mailed Jan. 9, 2008.

* cited by examiner

METHODS OF INSPECTING ROTARY DRILL BITS

CROSS-REFERENCE TO RELATED APPLICATIONS

This application claims the benefit of Provisional U.S. Patent Application Ser. No. 60/792,445 filed Apr. 17, 2006, the disclosure of which is incorporated herein in its entirety by this reference.

FIELD OF THE INVENTION

Embodiments of the present invention relate generally to apparatuses, systems, and methods for conducting nondestructive evaluation of rotary drill bits used for drilling subterranean formations to identify internal defects therein, and to rotary drill bits designed to facilitate nondestructive evaluation thereof. More specifically, such nondestructive evaluation may be conducted using ultrasound.

BACKGROUND

A typical rotary drill bit for drilling subterranean formations includes a bit body having a face region thereon carrying cutting structures for cutting into an earth formation. The bit body may be secured to a hardened steel shank having a threaded pin connection for attaching the drill bit to a drill string that includes tubular pipe segments coupled end to end between the drill bit and other drilling equipment. Equipment such as a rotary table or top drive may be used for rotating the drill string and drill bit. Alternatively, the shank may be coupled directly to the drive shaft of a down-hole motor to rotate the drill bit.

Generally, if the drill bit is a fixed-cutter, or so-called "drag" type rotary drill bit, the cutting structures on the face region of the bit body include a plurality of cutting elements formed at least in part of a superabrasive material such as polycrystalline diamond. Fixed-cutter rotary drill bits employing such polycrystalline diamond compact (PDC) cutting elements have been employed for several decades. Typically, the bit body of a rotary drill bit is formed from steel or a steel member embedded in a matrix material that includes hard particulate material, such as tungsten carbide (WC), infiltrated with a binder material such as a copper alloy.

In the case of steel body drill bits, the bit body typically is machined from stock material to the desired shape. Structural features may be defined at precise locations on the bit body by machining the bit body using a computer-controlled, multi-axis machine tool. Such structural features may include, for example, radially and longitudinally extending blades, cutting element pockets, ridges, lands, nozzle cavities, and drilling fluid courses and passages, including so-called "junk slots." Hard-facing is usually applied to the face region of the bit body and to other critical areas of the drill bit for resisting abrasion from contact with the formation being drilled and erosion by drilling fluid during drilling operations. The cutting elements generally are secured within pockets that are machined into blades located on the face region of the bit body. The hardened steel shank may be secured to the bit body after the bit body has been formed.

Matrix-type drill bits, on the other hand, include a bit body that is at least partially formed of hard particulate material such as tungsten carbide (WC) that is infiltrated with a binder material such as a copper alloy. Matrix-type drill bits generally are formed by filling a high-temperature mold formed of graphite or a ceramic material with particulate tungsten carbide and infiltrating the particles of tungsten carbide with molten copper alloy. However, because the matrix material generally is difficult or impossible to machine, part of a machinable steel blank typically is disposed within the mold prior to infiltration of the matrix material. The infiltrant binds the steel blank to the matrix material upon hardening to form a bit body that includes both the steel blank and the matrix material. Cast resin-coated sand, graphite displacements, or in some instances tungsten carbide particles in a flexible polymeric binder, may be employed to form internal as well as external structural features of the bit body. The machinable steel blank portion of a matrix-type bit body may be secured to a hardened steel shank in the same manner described previously in relation to steel body drill bits.

FIG. 1 illustrates a conventional matrix-type drill bit 10 formed generally according to the description above. The conventional matrix-type drill bit 10 includes a bit body 12 that is coupled to a steel shank 14. A bore 16 is formed longitudinally through a portion of the drill bit 10 for communicating drilling fluid to a face 20 of the drill bit 10 during drilling operations through a plurality of passages (not shown) extending from bore 16 to the face 20, wherein typically nozzles are disposed. Cutting elements 22 and 24 (typically diamond, and most often a PDC) may be bonded to the bit face during infiltration of the bit body if thermally stable PDCs, which are commonly referred to as thermally stable products, or TSPs, are employed. Alternatively, conventional, non-thermally stable PDC cutting elements 22 and 24 having diamond tables formed on WC substrates may be bonded by the substrates to the face 20 of the bit body 12 after the bit body 12 is formed by methods such as brazing, adhesive bonding, or mechanical affixation.

The bit body 12 includes a preformed steel blank 26 and a bit body matrix 28. The bit body matrix 28 may include particles of tungsten carbide bonded together by a copper alloy. The blank 26 may have a generally cylindrical or tubular shape or a fairly complex shape that includes features for structural reinforcement of, for example, blades formed on the bit face.

During formation of the bit body 12, the blank 26 may be positioned to extend partially within a high-temperature mold for casting the bit body 12. The blank 26 is affixed to the bit body matrix 28 upon solidification of the copper alloy binder material used to infiltrate the tungsten carbide particles. An exposed upper portion of the steel blank 26 then may be machined and affixed to the shank 14 by way of a threaded connection 30 as well as by a continuous, circumferential, or "girth" weld 32 formed between the assembled shank 14 and the blank 26. The shank 14 may include tapered threads 34 forming a pin connection at an upper portion thereof for connecting the matrix-type drill bit 10 to a string of drill pipe (not shown).

After a drill bit has been manufactured, it is typically used several times to perform successive drilling operations, during which the bit body may be subjected to extreme loads and stresses due to the applied weight on bit (WOB), the applied torque used to rotate the bit, and impact forces associated with contact of the bit and cutting elements carried thereon with the subterranean formation ahead of and surrounding the well bore. These stresses may generate a defect or a plurality of defects within the drill bit and may cause existing, latent defects to grow in size. The drill bit may fail catastrophically if the characteristics and magnitudes of the defects within the drill bit reach a critical point. Such characteristics may include the nature, size, location, and orientation of individual defects, and the number of defects within the drill bit. Thus, it would be advantageous to provide a method that may be used to nondestructively inspect a drill bit after its manufacture and between successive drilling operations to identify defects within the drill bit, to characterize the nature, size, location, orientation, and number of those defects.

BRIEF SUMMARY OF THE INVENTION

The present invention, in various embodiments, relates generally to apparatuses, systems, and methods for conducting nondestructive evaluation of rotary drill bits used for drilling subterranean formations to identify defects therein, and to rotary drill bits designed to facilitate nondestructive evaluation, such as ultrasonic inspection, thereof.

In some embodiments, the present invention includes methods for conducting nondestructive inspection of an earth-boring drill bit. The methods include communicating ultrasonic waves into the drill bit and detecting ultrasonic waves reflected by at least a portion of the drill bit. In some embodiments, the ultrasonic waves may be communicated into the drill bit from within a longitudinal bore of the drill bit. The reflected ultrasonic waves optionally may be detected from within the longitudinal bore of the drill bit. The methods may be used to confirm the presence or absence of one or more defects within a drill bit, and optionally may include generating a representation of at least a portion of the drill bit using the ultrasonic waves. Ultrasonic probes used in carrying out methods of the present invention may be configured as a single emitter/receiver combination, or as a phased array of emitters/receivers, both such configurations being known.

In additional embodiments, the present invention includes systems for ultrasonically inspecting an earth-boring drill bit. The systems include at least one ultrasonic probe, a longitudinal probe-positioning mechanism, a rotational probe-positioning mechanism, and a computer device, which may be used for at least one of controlling the emission of ultrasonic energy from the probe and receiving data or signals from the ultrasonic probe representative of reflected ultrasonic waves. The ultrasonic probe includes at least one ultrasonic transducer and may be configured for insertion within an internal longitudinal bore of the drill bit.

In yet additional embodiments, the present invention includes ultrasonic inspection apparatuses for inspecting a drill bit for drilling subterranean formations. The apparatuses include an ultrasonic probe, an ultrasonic probe support structure for supporting the ultrasonic probe, a longitudinal probe-positioning mechanism, and a rotational probe-positioning mechanism. A portion of the ultrasonic probe support structure may be configured for insertion into an internal longitudinal bore of a drill bit, and the ultrasonic probe may be coupled to that portion of the support structure and may be, itself, configured for insertion into an internal longitudinal bore of the drill bit.

Further embodiments of the invention include matrix-type drill bits for drilling subterranean formations that include a bit body defining an internal longitudinal bore therein. The bit body be configured to facilitate ultrasonic inspection of the bit body by, for example, reducing a number of material interfaces between an exterior surface of the drill bit and a region of the drill bit to be ultrasonically inspected. In some embodiments, the drill bits may comprise a bit body matrix coupled to a steel blank. The bit body matrix may adjoin the steel blank along an interface in a chamfer region, which may be oriented at an angle to a longitudinal axis of the bore. The steel blank may be configured to define at least a portion of the internal longitudinal bore wall and to provide a continuous path through the steel blank between the internal longitudinal bore and the chamfer region.

Still further embodiments of the present invention comprise rotary drill bits for drilling subterranean formations that include a shank and a bit body. The bit body defines an internal longitudinal bore therethrough circumscribed by an inner surface having a landing pad formed therein configured for facilitating substantially repeatable positioning of an ultrasonic probe within the longitudinal bore.

The features, advantages, and alternative aspects of the present invention will be apparent to those skilled in the art from a consideration of the following detailed description considered in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION OF THE INVENTION

Figure 1:
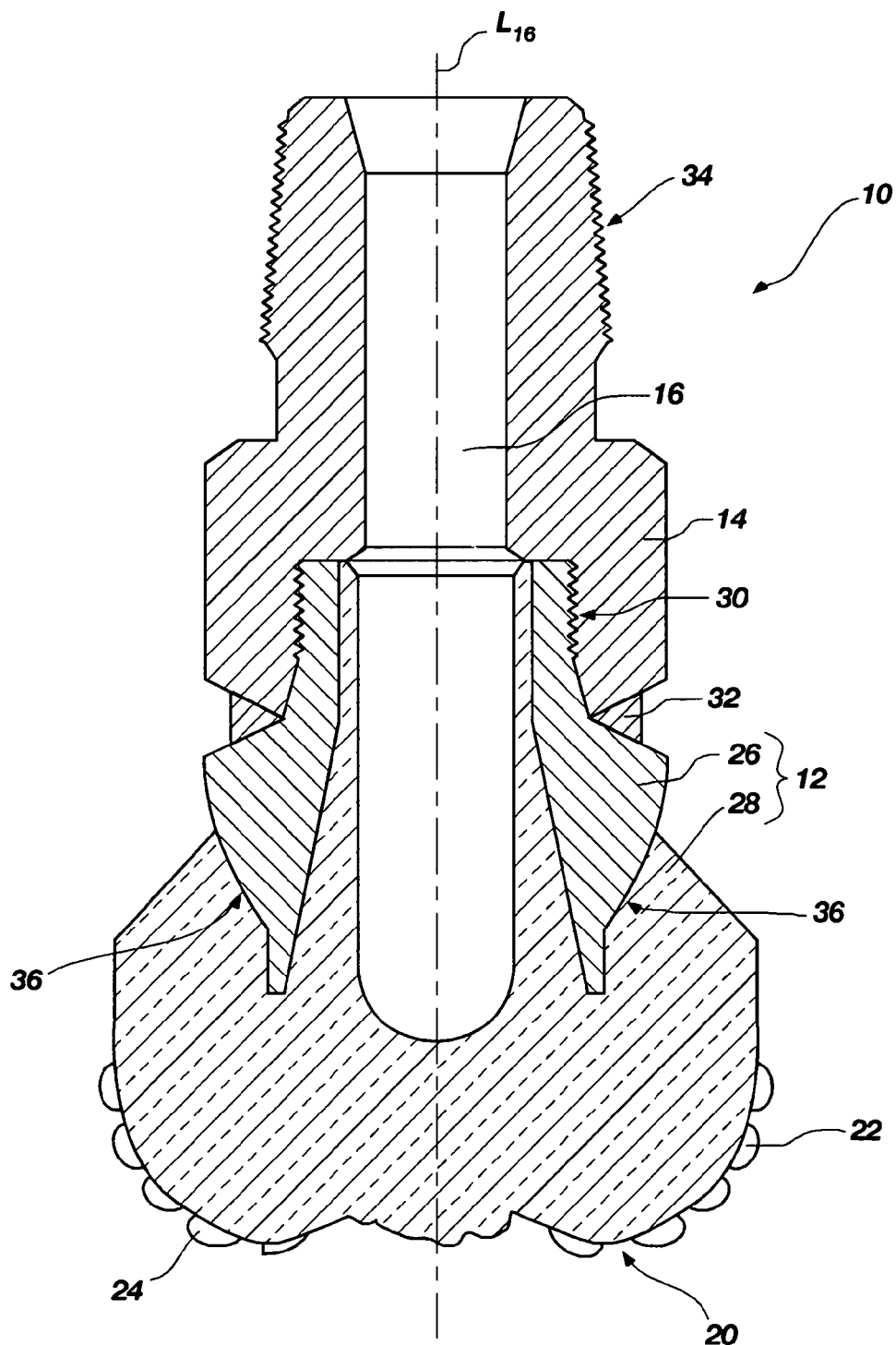
FIG. 1 is a cross-sectional view of a conventional matrix-type drill bit.

The present invention relates generally to apparatuses, systems, and methods for conducting nondestructive evaluation of rotary drill bits used for drilling subterranean formations to identify defects therein, and to rotary drill bits designed to facilitate nondestructive evaluation, such as ultrasonic inspection, thereof.

The illustrations presented herein are not meant to be actual views of any particular apparatus, system, or method for conducting nondestructive evaluation of rotary drill bits, but are merely idealized representations which are employed to describe the present invention. Additionally, elements and features common between drawing figures and embodiments may retain the same numerical designation.

According to the present invention, systems and methods may be used for performing ultrasonic, nondestructive evaluation or inspection of a drill bit after the drill bit has been manufactured before its first use in drilling operations, as well as between successive drilling operations, in which the drill bit is to be employed. FIG. 2 illustrates a non-limiting example of an ultrasonic inspection system 50 according to the present invention and that may be used to conduct nondestructive, ultrasonic evaluation of drilling equipment, such as the conventional matrix-type drill bit 10 shown in FIG. 1. The ultrasonic inspection system 50 as shown in FIG. 2 is configured for inspection of the matrix-type drill bit 10 although, as noted below, the invention is not limited to inspection of matrix-type drill bits, or to drill bits per se. The matrix-type drill bit 10 is shown in FIG. 2 to include defects 40 proximate the so-called chamfer regions 36 between the blank 26 and the bit body matrix 28. It has been observed by the inventors of the present invention that defects within conventional matrix-type drill bits such as drill bit 10 may form proximate these chamfer regions 36. Of course, defects also may form or develop at any region of or within a drill bit, without limitation. For example, voids and cracks may be present wholly within the bit body matrix 28, as well as wholly within blank 26.

The ultrasonic inspection system 50 may include a rotary table 52 for supporting the drill bit 10. Rotary table 52 may be manually rotatable, or driven by, for example, an electric motor through a gear drive or a rotary stepper motor for precise control of rotational position of the rotary table 52 and, consequently, of a drill bit 10 carried thereon. Alternatively, another, less precise type of rotational drive may be employed in combination with a rotary encoder for precise tracking of rotational position of the rotary table 52. A drill bit alignment structure 54 may be provided on rotary table 52 for aligning the longitudinal axis $L_{16}$ of the bore 16 of drill bit 10 with the axis of rotation of the rotary table 52. In one embodiment of the present invention, the drill bit alignment structure 54 may include, for example, structural features having contours or shapes that are complementary to contours or shapes of structural features of the face 20 (FIG. 1) of the drill bit 10 so as to securely support drill bit 10 on its face 20 in a desired position and orientation for rotation.

The ultrasonic inspection system 50 also may include an ultrasonic probe 56 having at least one ultrasonic transducer configured for emitting and detecting ultrasonic waves. The ultrasonic probe 56 may have cross-sectional dimensions less than the cross-sectional dimensions of the bore 16 and, accordingly, may be sized and configured to fit within the bore 16 of the drill bit 10. In addition, the ultrasonic probe 56 may have cross-sectional dimensions small enough to provide a selected near field standoff distance between an ultrasonic wave emitting and receiving surface of the ultrasonic probe 56 and a facing interior surface of the drill bit 10 within the bore 16. Providing a selected near field standoff distance between an emitting and receiving surface of the ultrasonic probe 56 and an interior surface of the drill bit 10 may minimize noise in the electrical signals generated by the ultrasonic transducer of ultrasonic probe 56 responsive to ultrasonic waves reflected due, at least in part, to roughness of the interior surface of bore 16. A suitable near field standoff distance, as will be recognized by those of ordinary skill in the art, will depend on the operational frequency of the ultrasonic probe 56 selected. It is believed that a near field standoff distance of, for example, nineteen millimeters between an emitting and receiving surface of the ultrasonic probe 56 and an interior surface of the drill bit 10 within the bore 16 will be adequate with most ultrasonic probes. One suitable ultrasonic probe for implementing the present invention is a Focus 32/64 ultrasonic Phased Array Pulser-Receiver, operable at a frequency of 5 MHz, with 64 transducer elements in the array and an element pitch (spacing) of 0.60 mm.

The ultrasonic inspection system 50 also may include a probe support structure 60 for positioning and supporting the ultrasonic probe 56 within the bore 16 of the drill bit 10. The probe support structure 60 may include a cantilevered support member 64 vertically movably coupled to a stationary member 62, shown for convenience as a vertical column, by a longitudinal positioning mechanism 66, shown schematically as a collar. The cantilevered support member 64 may include a laterally extending portion secured at one end to longitudinal positioning mechanism 66 and having at an opposing end a longitudinally extending portion that extends substantially at a right angle thereto. The longitudinally extending portion of the movable member 64 carries ultrasonic probe 56 at its free end. The longitudinal positioning mechanism 66 may be used to move the cantilevered support member 64 and, thus, ultrasonic probe 56, in a generally longitudinal direction relative to the drill bit 10 and parallel to longitudinal bore 16. The longitudinal positioning mechanism 66 may comprise, for example, a manually operated gear set or an electromechanical device comprising an electrically driven gear set to be cooperative with teeth on stationary member 62, a stepper motor cooperative with stationary member 62, a pneumatically or hydraulically driven piston cooperative with a bore defined by stationary member 62. In addition, the longitudinal positioning mechanism 66 may comprise a hand-operated clamp associated with a collar for vertically positioning cantilevered support member 64. Use of a manual or powered drive mechanism in longitudinal positioning mechanism 66 may be in association with a linear position sensor if the drive mechanism itself does not provide a signal or other output indicative of the vertical position of movable member 64 and, thus, of ultrasonic probe 56 carried thereby.

It is also contemplated that, in lieu of the use of a rotary table 52, the longitudinally extending portion of cantilevered support member 64 may comprise a separate component from the laterally extending portion thereof, and the longitudinally extending portion rotatably mounted to the free, or distal end of the lateral portion. Thus, ultrasonic probe 56 may be rotated within longitudinal bore 16 rather than drill bit 10 being rotated. A sensor may be used to monitor the rotational position of ultrasonic sensor and, if desired, the coupling between the longitudinal and lateral portions of cantilevered support member 64 or between ultrasonic probe 56 and the longitudinal portion of cantilevered support member 64 may include structure, for example, slip ring contacts, to permit rotation of ultrasonic probe 56 through an arc greater than 360° or a plurality of full rotations.

The ultrasonic inspection system 50 also may include a computer device (not shown) for operating the ultrasonic probe 56 and for receiving, storing, analyzing, graphing, or otherwise manipulating data generated by the ultrasonic probe 56 in response to ultrasonic waves. For example, a commercially available portable computer device specifically designed for ultrasonic testing that may be used with the ultrasonic inspection system 50 is sold under the trademark OMNISCAN™ by RID Tech of Quebec, Canada. Alternatively, a personal computer may be used in conjunction with software appropriate for acquiring and analyzing ultrasound data. Exemplary commercially available software that may be used in conjunction with a personal computer is also sold by Olympus NDT Inc., of Waltham, Mass. Such device and software are suitable for use with a phased array ultrasonic probe. An ultrasonic pulser and receiver (not shown) also may be used in conjunction with the computer device and the ultrasonic probe 56 to facilitate control and operation of the ultrasonic probe 56 by the computer device.

In additional embodiments, the ultrasonic probe 56 may be manually operated without the use of a computer device, and an analog signal generated thereby may be visually analyzed (without the use of a computer device) to perform ultrasonic inspection of the drill bit 10.

Electrical cables (not shown) may be provided as necessary between the computer device and the ultrasonic probe 56 for transmitting electrical signals therebetween. The electrical cables may be coupled to the laterally extending portion and the longitudinally extending portion of the cantilevered support member 64. If the cantilevered support member 64 is hollow, the electrical cables may extend within the moveable cantilevered support member 64 to ultrasonic probe 56.

As noted previously, the rotary table 52 may include a sensor or other device for indicating a relative rotational position of the rotary table 52 (and thus of a drill bit 10 resting thereon) at any given time, or used to indicate relative rotational position of ultrasonic probe 56 if rotary table 52 is not employed. Similarly, and also as previously noted, the longitudinal positioning mechanism 66 may include a sensor or other device for indicating the longitudinal position of the cantilevered support member 64 and, correspondingly, the ultrasonic probe 56 at any given time. These sensors may be connected to the computer device and the outputs (signals) therefrom used to determine a position of the ultrasonic probe 56 relative to the drill bit 10 and to correlate ultrasonic data acquired at any given time to a given region, in terms of longitudinal and circumferential location thereof, within the drill bit 10. Such data may also be used to generate a three-dimensional representation of the interior of the drill bit 10 as noted below, or develop a two-dimensional (X-Y axis) section therethrough along, for example, any selected diameter of drill bit 10.

It will be appreciated that rotary and longitudinal position sensors, such as rotary and linear encoders, are desirably used in combination with ultrasonic probe 56 by providing feedback to facilitate precise correlation of the rotational and longitudinal position of the ultrasonic probe 56 with signals produced by ultrasonic probe 56 corresponding to ultrasonic waves received by ultrasonic probe after reflection from within the body of drill bit 10. Thus, the positional signals correlated with the ultrasonic probe 56 signals may be used to develop the aforementioned three-dimensional representation of the interior of the drill bit 10 or a two-dimensional section therethrough, to identify internal defects within drill bit 10.

To conduct ultrasonic inspection of the drill bit 10 using the ultrasonic inspection system 50 shown in FIG. 2, the cantilevered support member 64 and ultrasonic probe 56 may be moved using the longitudinal positioning mechanism 66 upwardly to a position that allows the drill bit 10 to be placed on the rotary table 52. The drill bit 10 may be positioned on the rotary table 52 using the drill bit alignment structure 54 such that the longitudinal axis $L_{16}$ of the bore 16 substantially coincides with the axis of rotation of the rotary table 52. The cantilevered support member 64 and the ultrasonic probe 56 may then be moved using the longitudinal positioning mechanism 66 to position the ultrasonic probe 56 at a selected location within the bore 16 of the drill bit 10. An ultrasonic couplant 68 such as water or other suitable fluid or gel may be provided in the bore 16 of the drill bit 10 to ultrasonically couple the ultrasonic probe 56 to the drill bit 10. Since drilling fluid courses typically are provided within the drill bit 10 to extend from the bore 16 to the face 20 thereof, the drill bit 10 may be submerged in a water tank (not shown) carried on rotary table 52 to prevent the ultrasonic couplant 68 from draining out from the bore 16 during ultrasonic evaluation of the drill bit 10. Alternatively, the drilling fluid course openings may be plugged proximate the face of drill bit 10 with, for example, elastomeric plugs prior to filling the bore 16 with the ultrasonic couplant 68. The drill bit alignment structure 54 also may be configured to plug openings communicating between the bore 16 and the exterior of the drill bit 10 when the drill bit 10 is positioned on the drill bit alignment structure 54. Such a drill bit alignment structure 54 may be configured for use with a specific design and size of bit and include, for example, a layer of elastomeric material configured for covering the openings in the face of the drill bit 10 or including protruding structural features, which may be formed of or covered with an elastomeric material for being received in and plugging openings in the drill bit 10 proximate a supporting surface of the drill bit alignment structure 54.

In additional embodiments, at least a portion of the rotary drill bit 10 may be immersed in an ultrasonic couplant, or an ultrasonic couplant, such as a gel, may be applied directly to the ultrasonic probe 56 or to a surface of the drill bit 10 within the bore 16 to facilitate ultrasonic inspection thereof.

Ultrasonic waves 59 then may be emitted or pulsed by the ultrasonic probe 56 and communicated or directed into at least a region of the drill bit 10. These ultrasonic waves 59 may be reflected by structures or features, including any defect or defects, within the drill bit 10. These reflected ultrasonic waves may be detected using the ultrasonic probe 56 and converted by ultrasonic probe 56 into electrical signals. Data resident in or carried by the electrical signals generated by the ultrasonic probe 56 may be received, stored, analyzed, graphed, mapped or otherwise manipulated using the computer device, in combination with rotational and longitudinal positional data for ultrasonic probe 56 for each reflected ultrasound data set. If present within the drill bit 10, at least one defect, such as the exemplary defects 40 within the drill bit 10 shown in FIG. 2, may reflect or cause refraction of, or both, at least a portion of the ultrasonic waves in a manner aberrational in comparison to, or inconsistent with, homogeneous regions within drill bit or known boundary surfaces and boundary surface configurations between regions. In this manner, at least the presence or absence of at least one defect 40 within the drill bit 10 may be indicated by the data acquired using the ultrasonic probe 56.

It should be recognized that refraction, reflection, or a combination of refraction and reflection of ultrasonic waves may occur at an interface between materials having different physical properties. For example, refraction, reflection, or a combination of refraction and reflection of ultrasonic waves may occur at the interface between the ultrasonic couplant 68 and the bit body matrix 28 and at the interfaces between the bit body matrix 28 and the blank 26. The reflection, or refraction or bending, of the ultrasonic waves in the aforementioned aberrational manner may result in the detection of defects at locations longitudinally above or below the position at which the ultrasonic transducer is located. Snell's law may be considered and used to determine the path of the ultrasonic waves 59 if the speeds of the ultrasonic waves in each material of the drill bit (for example, steel blank, one or more matrix materials, weld material) and the angles of the interfaces between different materials with respect to the incident ultrasonic waves are known. Thus, a three-dimensional computer model of a given drill bit 10, including the various regions of the drill bit 10 and boundary locations therebetween, may be used in conjunction with the refracted and reflected ultrasonic waves to determine the nature, size, location, orientation, and number of any defects by comparing magnitudes, angles and resulting patterns of reflected ultrasonic waves detected during inspection of the drill bit 10 with an idealized model of that given size and design of drill bit, or with actual data from another drill bit of the same size and design and known to be defect-free. In other words, the inspection techniques of the present invention may be most beneficially utilized in conjunction with specific bit designs, materials, sizes of bit body components, and interfaces between the components.

It should be recognized that ultrasonic inspection of rotary drill bits 10 may be performed according to the present invention using longitudinal waves, shear waves, or both. As known in the art, longitudinal waves typically are used for normal incidence inspection techniques and shear waves typically are used for oblique incidence inspection techniques. The use of shear waves or longitudinal waves may be dictated by the chamfer angle between the blank and the matrix material or materials of the bit body.

The computer device may be used to detect and record a longitudinal position of the ultrasonic probe 56 and a rotational orientation of the rotary table 52 using the corresponding, associated sensors. The rotary table 52 may be selectively rotated, as by a selected increment (for example, 1°) and ultrasonic waves may again be communicated into another internal segment of the drill bit 10, and reflected ultrasonic waves may be detected. Such a process may be repeated as necessary or desirable for inspecting a selected region or volume of the drill bit 10. For example, this process may be performed until a substantially complete 360° ultrasonic scan of the drill bit 10 has been completed at a first longitudinal position of the ultrasonic probe 56. The ultrasonic probe 56 then may be selectively moved in a longitudinal direction by a selected increment (for example, 0.040 inch) within longitudinal bore 16 relative to the drill bit 10, and another substantially complete 360° ultrasonic scan of the drill bit 10 may be obtained at the new longitudinal position. This process may be repeated until a desired region or volume of the drill bit 10 has been ultrasonically inspected. Alternatively, the rotary table 52 may be selectively rotated while the ultrasonic probe 56 is selectively moved in a longitudinal direction to provide a helical scan path for the ultrasonic probe 56 while acquiring data. In such an instance, it may be desirable to dispose an ultrasonic probe 56 having a plurality of transducers, for example two or four transducers at equal circumferential spacing (180° or 90°, respectively, see FIG. 4 below), at the distal end of cantilevered support member 64 to obtain adequate data while moving cantilevered support member more rapidly through longitudinal bore 16 or to avoid the need for rotation of drill bit 10. Further, it may be desirable to control drive mechanisms for longitudinal movement of cantilevered support member 64 and rotary table 52 using a computer device for coordinated movement thereof to ensure a complete scan of drill bit 10 which does not omit any significant regions thereof.

The ultrasonic data acquired at a plurality of longitudinal positions of the ultrasonic probe 56 and a plurality of rotational positions of the rotary table 52 may be combined and analyzed by the computer to generate a virtual three-dimensional representation of at least a portion of the drill bit 10. The data and the virtual three-dimensional representation of the drill bit 10 may be used to identify and characterize any defect or defects present within the drill bit 10. In this manner, the ultrasonic inspection system 50 may be used to identify defects within the drill bit, to characterize the nature, size, location, orientation, and number of those defects, to allow removal of the drill bit from service when the characteristics of those defects reach a critical point, and thereby to prevent catastrophic failure of the drill bit during a drilling operation.

It should be noted that precise identification of the nature, size, location, orientation, and number of defects within a given drill bit 10 is enhanced by use of a reference calibration feature or standard which may be manufactured intrinsic to each drill bit 10 to facilitate inspection thereof. Such a reference calibration feature may comprise, for example, a 0.25 inch long, 0.0010 to 0.0050 inch deep circumferential recess machined into an interior surface of blank 26. A bit design such as that disclosed below with respect to FIG. 6, wherein the interior surface of blank 26 defines an interior surface of longitudinal bore 16, is particularly suitable for providing such a reference calibration feature, as ultrasonic waves emitted from probe 56 will pass through ultrasonic couplant 68 and impinge upon the surface of the recess, reflecting back from a known and precise distance between the face of ultrasonic probe 56 and the recess surface, which may be used to calibrate ultrasonic probe at the beginning of, or at intervals during, an inspection operation. Further, such a calibration surface may be located elsewhere on blank 26, such as at an interface surface between blank 26 and matrix material, so that passage, for example, of ultrasonic waves through a known thickness of steel may be calibrated. Furthermore, a plurality of reference calibration features may be provided at various known depths and locations on or in a drill bit. Such a configuration may facilitate real-time calibration as the drill bit is inspected for defects as previously described herein. In other words, calibration may be performed periodically using each of a series of calibration features as the drill bit is ultrasonically scanned. Such calibration features may be designed so as not to negatively affect performance of the drill bit. In additional embodiments, a portable reference standard may be secured to the ultrasonic probe 56 over the emitting and receiving face thereof in the presence of ultrasonic couplant 68 to provide a known reflective standoff distance, and the probe 56 operated in a calibration mode before insertion into longitudinal bore 16. In any case, the amplitude of a response against a known standard may be employed to scale the size and configuration of a located defect.

Figure 2:
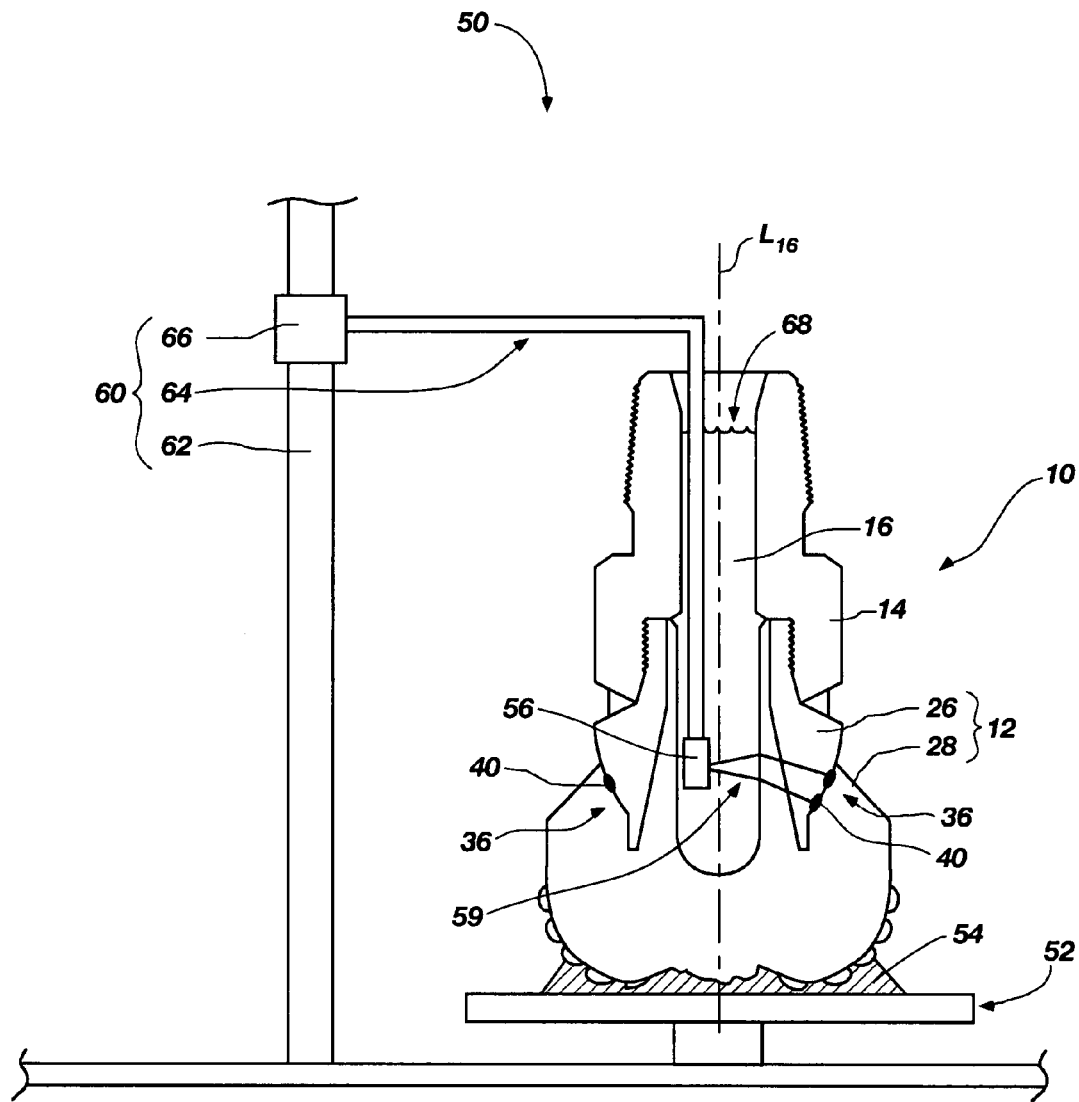
FIG. 2 is a partial cross-sectional schematic view of a system according to an embodiment of the present invention and that may be used to conduct nondestructive ultrasonic evaluation of a drill bit.
Figure 3:
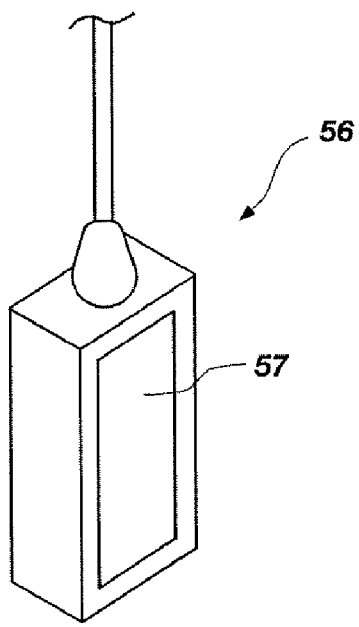
FIG. 3 is a perspective view of an embodiment of an ultrasonic probe according to the present invention.
Figure 4:
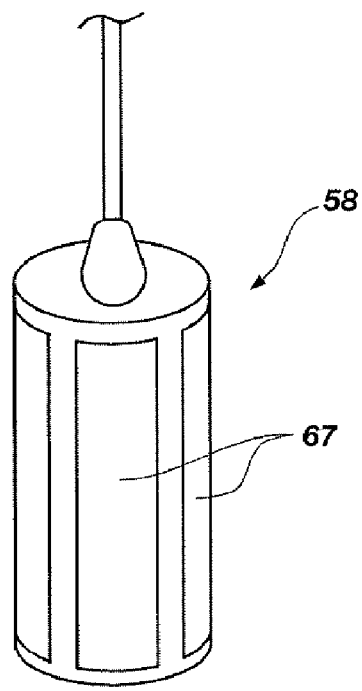
FIG. 4 is a perspective view of another embodiment of an ultrasonic probe according to the present invention.

Ultrasonic probes and software for operating ultrasonic transducers within the ultrasonic probes and for analyzing and graphing the data collected by the probes are known in the art and are commercially available, as noted above. FIG. 3 is an enlarged perspective view of the ultrasonic probe 56 shown in FIG. 2. The ultrasonic probe 56 has a rectangular shape and contains an active surface 57 that may include a phased array of ultrasonic transducers (not shown). An alternative ultrasonic probe 58 is shown in FIG. 4 that has a cylindrical shape and that may be used in the ultrasonic inspection system 50 shown in FIG. 2. The ultrasonic probe 58 may include a plurality of active surfaces 67 arranged about the circumference of the ultrasonic probe 58. Each active surface 67 of the ultrasonic probe 58 may include a phased array of ultrasonic transducers (not shown). In this configuration, the ultrasonic probe 58 may be configured to perform a substantially complete 360° ultrasonic scan of the drill bit 10 corresponding to a given longitudinal location within the bore 16 of the drill bit 10 without rotating the drill bit 10 relative to the ultrasonic probe 56.

Due to the complexity of the manufacturing processes used to construct conventional matrix-type drill bits such as drill bit 10, the longitudinal axis $L_{16}$ of the bore 16 may not precisely coincide with a longitudinal axis of the drill bit 10. In other words, the bore 16 may not be precisely centered or oriented within the drill bit 10. If the longitudinal axis $L_{16}$ of the bore 16 does not coincide with the longitudinal axis of the drill bit 10, the ultrasonic probe 56 may be positioned relative to the longitudinal axis $L_{16}$ of the bore 16. This may facilitate providing a selected standoff distance between a surface of the ultrasonic probe 56 and an interior surface of the drill bit 10 as the drill bit 10 is rotated relative to the ultrasonic probe 56. This may facilitate accurate determination of a location of any defect or defects within the drill bit 10 as indicated by data acquired from the ultrasonic probe 56. At least in part for this reason, a drill bit alignment structure 54 as previously referenced herein may be provided for aligning the longitudinal axis $L_{16}$ of the bore 16 of drill bit 10 with the axis of rotation of the rotary table 52.

The ultrasonic inspection system 50 may include an additional measuring mechanism (not shown) for accurately determining the location and orientation of a longitudinal axis $L_{16}$ of the bore 16 of the drill bit 10. This additional measuring mechanism may include a metrology device such as, for example, a coordinate measuring machine (CMM). The coordinate measuring mechanism may be used to identify the locations of several points on the interior surface of the drill bit 10 within the bore 16, and using those locations, identify the position and orientation of the bore 16 and the longitudinal axis $L_{16}$ thereof. Once the position and orientation of the longitudinal axis $L_{16}$ has been determined, the drill bit 10 may be positioned on the rotary table 52 such that the axis of rotation of the rotary table 52 substantially coincides with the longitudinal axis $L_{16}$ of the bore 16. The drill bit alignment structure 54 may be used to facilitate this process.

Figure 5:
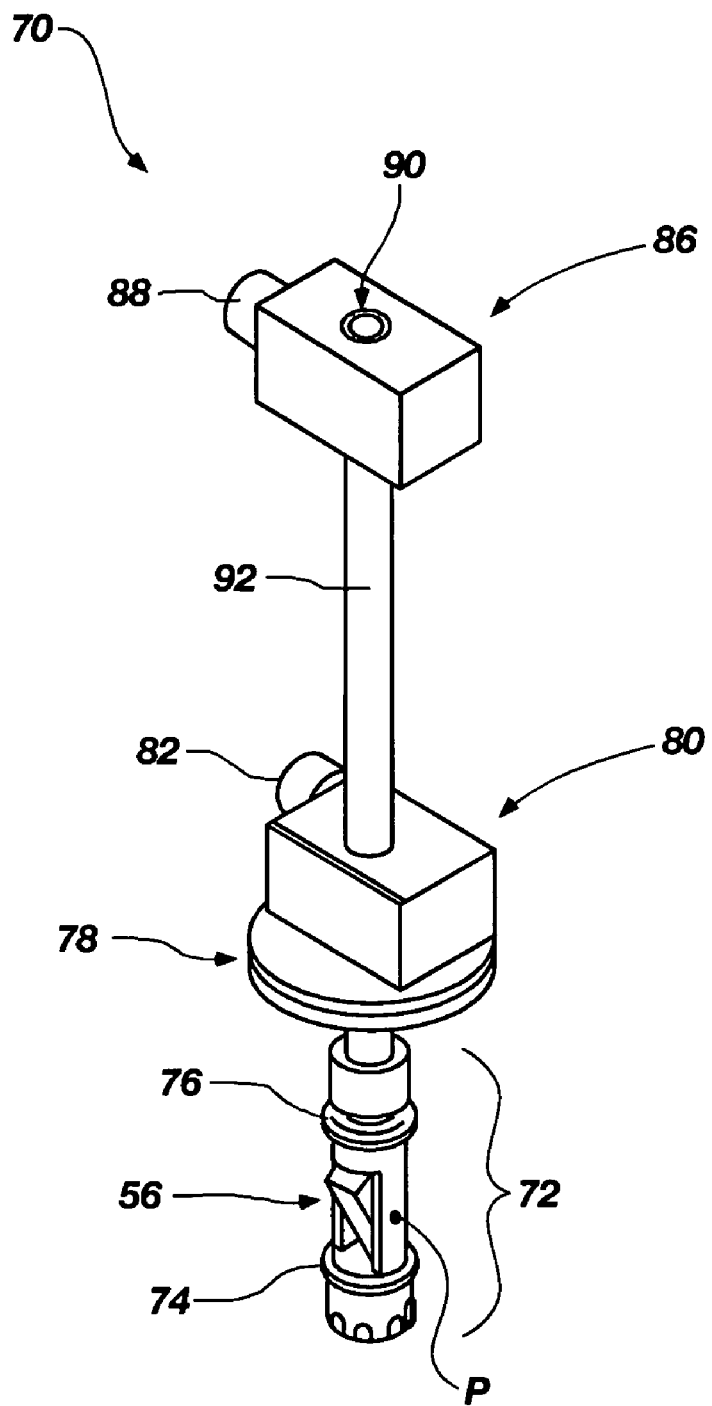
FIG. 5 is a perspective view of an apparatus according to an embodiment of the present invention and that may be used to conduct nondestructive ultrasonic evaluation of a drill bit.

FIG. 5 illustrates a portable exemplary ultrasonic inspection apparatus 70 according to an embodiment of the present invention that may be used to conduct nondestructive, ultrasonic inspection of drilling equipment, such as the conventional matrix-type drill bit 10 shown in FIG. 1. The ultrasonic inspection apparatus 70 may include a lower portion 72 that is configured to be positioned within the bore 16 of the drill bit 10. The lower portion 72 may include an ultrasonic probe 56, which may be positioned between a lower elastomeric o-ring 74 and an upper elastomeric o-ring 76. During use, the lower elastomeric o-ring 74 and the upper elastomeric o-ring 76 may sealingly engage the interior surface of the drill bit 10 within the bore 16. A disc-shaped collar 78 may be provided to engage a surface of the shank 14 when the lower portion 72 is disposed within the bore 16 of the drill bit 10. The disc shaped collar 78 may be configured to anchor and center the ultrasonic inspection apparatus 70 to the drill bit 10. For example, the disc shaped collar 78 may include tapered threads on an interior surface thereof (not shown) for connecting the disc shaped collar 78 to the tapered threads 34 of the shank 14 shown in FIG. 1.

The ultrasonic inspection apparatus 70 may include a longitudinal positioning mechanism 80 for selectively moving the lower portion 72 and the ultrasonic probe 56 in a longitudinal direction relative to the drill bit 10. The longitudinal positioning mechanism 80 may include a sensor 82 for identifying a longitudinal position of the ultrasonic probe 56 relative to the drill bit 10 at any given time. The ultrasonic inspection apparatus 70 also may include a rotational positioning mechanism 86 for selectively rotating the lower portion 72 and the ultrasonic probe 56 relative to the drill bit 10. The rotational positioning mechanism 86 may include a sensor 88 for identifying a rotational position of the ultrasonic probe 56 relative to the drill bit 10 at any given time. The longitudinal positioning mechanism 80 and the rotational positioning mechanism 86 may include electro-mechanical devices, mechanical devices, pneumatic devices, or hydraulic devices for selectively moving the ultrasonic probe 56 in a longitudinal direction relative to the drill bit 10 and for selectively rotating the ultrasonic probe 56 relative to the drill bit 10. For example, the longitudinal positioning mechanism 80 and the rotational positioning mechanism 86 each may include an electrical motor for adjusting the longitudinal and rotational position of the ultrasonic probe 56 within the bore 16 of the drill bit 10. The electrical motors may be controlled by a computer device to further automate the inspection of a drill bit. Alternatively, the longitudinal positioning mechanism 80 and the rotational positioning mechanism 86 may be hand-operated.

An opening 90 may be provided at the top of the ultrasonic inspection apparatus 70 that communicates with the interior cavity of a hollow longitudinal support member 92 that is coupled to the lower portion 72. When the lower portion 72 of the ultrasonic inspection apparatus 70 is inserted into the bore 16 of a drill bit, an ultrasonic couplant such as water may be introduced through an aperture in the wall of hollow longitudinal support member 92 into the region between the lower elastomeric o-ring 74 and the upper elastomeric o-ring 76 within the bore 16 of the drill bit 10 through the opening 90 and the hollow longitudinal support member 92.

The ultrasonic probe 56 may be pivotably coupled to the lower portion 72 of the ultrasonic inspection apparatus 70 about an axis transverse to hollow longitudinal support member 92 using a pin support P as shown in FIG. 5. An adjustment mechanism may be provided for adjusting an angle of the ultrasonic probe 56 upward and downward relative to a plane perpendicular to the longitudinal axis $L_{16}$ of the bore 16. For example, a wire or cable may be provided through the opening 90 and through the longitudinal support member 92 to the ultrasonic probe 56. By allowing the ultrasonic probe 56 to pivot about an axis perpendicular to and within the bore 16 of the drill bit 10, the ultrasonic waves emitted thereby may be directed into the drill bit 10 at various angles relative to the plane perpendicular to the longitudinal axis thereof. An additional sensor (not shown) may be provided to indicate an angle of the pivotably mounted ultrasonic probe 56 at any given time.

A computer device (not shown) may be used with the ultrasonic inspection apparatus 70 in the same manner as discussed previously in relation to the ultrasonic inspection system 50 shown in FIG. 2 to control the ultrasonic probe 56 and to receive, store, analyze, graph, or otherwise manipulate data generated by the ultrasonic probe 56 in response to ultrasonic waves. Electrical cables and wires may be provided between the computer device and the ultrasonic probe 56 for transmitting electrical signals therebetween. The electrical cables may extend through the opening 90 and the longitudinal support member 92 to the ultrasonic probe 56.

The ultrasonic inspection apparatus 70 may be used to conduct ultrasonic inspection of the drill bit 10 in a similar manner as that discussed previously in relation to the ultrasonic inspection system 50 shown in FIG. 2. Particularly, the lower portion 72 of the ultrasonic inspection apparatus 70 may be positioned within the longitudinal bore 16 of the drill bit 10 such that the disc-shaped collar 78 engages the shank 14 of the drill bit 10. The lower portion 72 may be moved in a longitudinal direction relative to the drill bit 10 to a selected position using the longitudinal positioning mechanism 80. An ultrasonic couplant such as water may be provided through the opening 90 to the region between the lower elastomeric o-ring 74 and the upper elastomeric o-ring 76 within the bore 16 of the drill bit 10.

Ultrasonic waves then may be emitted or pulsed from the ultrasonic probe 56 and communicated or directed into the drill bit 10. Reflected ultrasonic waves may be detected using the ultrasonic probe 56. Electrical signals generated by the ultrasonic probe 56 may be received and recorded by the computer device. The computer device also may detect and record the longitudinal position of the ultrasonic probe 56, the rotational orientation of the ultrasonic probe 56, and the angle of the ultrasonic probe 56 relative to the drill bit 10 as indicated by the corresponding sensors. This information may be used to correlate the acquired ultrasonic data to a particular location or region within the drill bit 10.

The lower portion 72 and the ultrasonic probe 56 may be selectively rotated and ultrasonic waves may again be communicated into the drill bit 10 and reflected ultrasonic waves may be detected and recorded. This process may be repeated until a substantially complete 360° ultrasonic scan of the drill bit 10 has been completed at a longitudinal position of the ultrasonic probe 56 with respect to the drill bit 10. The ultrasonic probe 56 then may be selectively moved in a longitudinal direction relative to the drill bit 10 and another substantially complete 360° ultrasonic scan of the drill bit 10 obtained at a different longitudinal position. This process may be repeated until a desired region or volume of the drill bit 10 has been ultrasonically evaluated. The recorded ultrasonic data for a plurality of longitudinal and rotational positions of the ultrasonic probe 56 may be combined and analyzed by the computer device to generate a virtual three-dimensional representation of at least a region of the drill bit 10. The data and the virtual three-dimensional representation of the at least a portion of the drill bit 10 may be used to indicate the presence of a defect or defects within the drill bit 10. In this manner, the ultrasonic inspection apparatus 70 may be used to identify defects within a drill bit, to characterize the nature, size, location, orientation, and number of those defects, to allow removal of the drill bit from service when selected characteristics of those defects reach a critical point, and thereby to prevent catastrophic failure of the drill bit during a drilling operation.

As discussed previously herein, refraction and reflection of ultrasonic waves generated by the ultrasonic probe 56 may occur (for example) at an interface between the ultrasonic couplant 68 and the bit body matrix 28, and at interfaces between the bit body matrix 28 and the blank 26. The refraction or bending of the ultrasonic waves may complicate precisely determining the position of any detected defect within the drill bit 10. In another aspect of the present invention, drill bits may be designed to minimize the number of interfaces between the ultrasonic probe and the chamfer regions 36 at which a defect may be likely to occur to reduce the amount of refraction and reflection that occurs at interfaces and to further improve the accuracy of the inspection techniques described herein.

Figure 6:
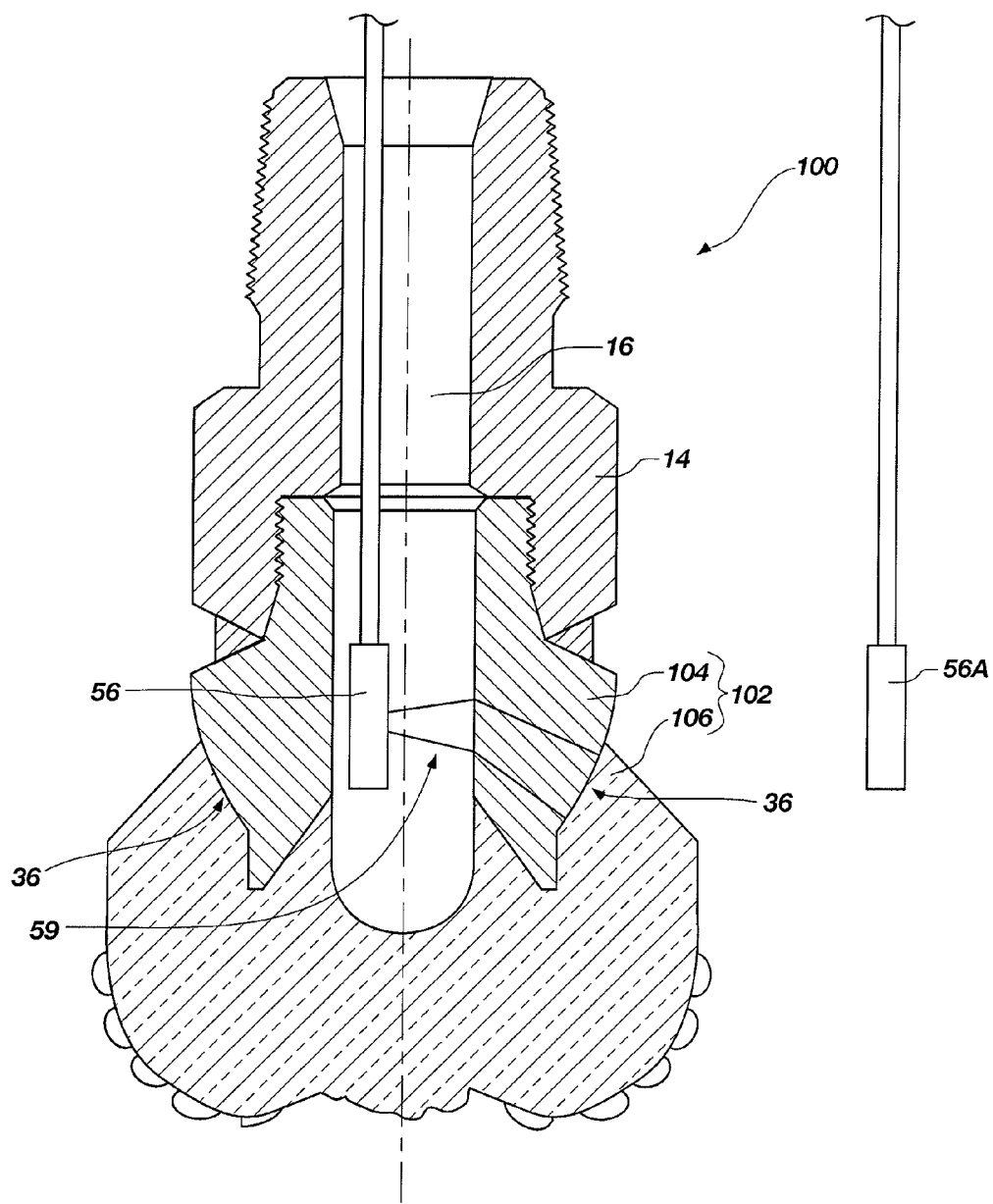
FIG. 6 is a cross-sectional view of a matrix-type drill bit according to an embodiment of the present invention and that is configured to facilitate nondestructive ultrasonic evaluation thereof.

For example, a matrix-type drill bit 100 according to an embodiment of the present invention is shown in FIG. 6. The drill bit 100 is similar to the drill bit 10 shown in FIG. 1 and includes a bit body 102 and a shank 14. A longitudinally extending bore 16 is provided through the drill bit 100. The bit body 102 also includes a steel blank 104 and a bit body matrix 106. In contrast to the drill bit 10 shown in FIG. 1, however, the steel blank 104 of the drill bit 100 shown in FIG. 6 extends radially inwardly to the interior wall of bore 16 in the regions of the bit body 102 near the chamfer regions 36 at which defects may occur. As illustrated by comparison to a conventional matrix-type drill bit such as drill bit 10 shown in FIG. 1, an interface between the bit body matrix 106 and the steel blank 104 has been eliminated to provide a continuous path through the steel blank 104 between the longitudinal bore 16 and the chamfer regions 36 in this configuration of the drill bit 100. The overall refraction or bending of ultrasonic waves 59 therefore may be reduced and the ability to accurately determine the position and orientation of defects within the bit body 102 may be facilitated.

Systems and apparatuses according to embodiments of the present invention, such as the ultrasonic inspection system 50 and the ultrasonic inspection apparatus 70, may be used to monitor an existence, development, or both of at least one defect within a drill bit over a given time period. For example, successive evaluations of a drill bit may be performed after each drilling operation and may be compared to one another. The ability to repeatedly position an ultrasonic probe at substantially the same location within the bore of a drill bit may be relatively desirable for ensuring that the results of successive evaluations of a drill bit may be fairly compared. In order to enable relatively precise repositioning of the ultrasonic probe within a drill bit, the interior of the drill bit may be configured to provide a landing pad or other reference feature or location for the transducer. The landing pad may allow for substantially repeatable placement of the ultrasonic probe within the bore of the drill bit each time the drill bit is to be inspected.

Figure 7:
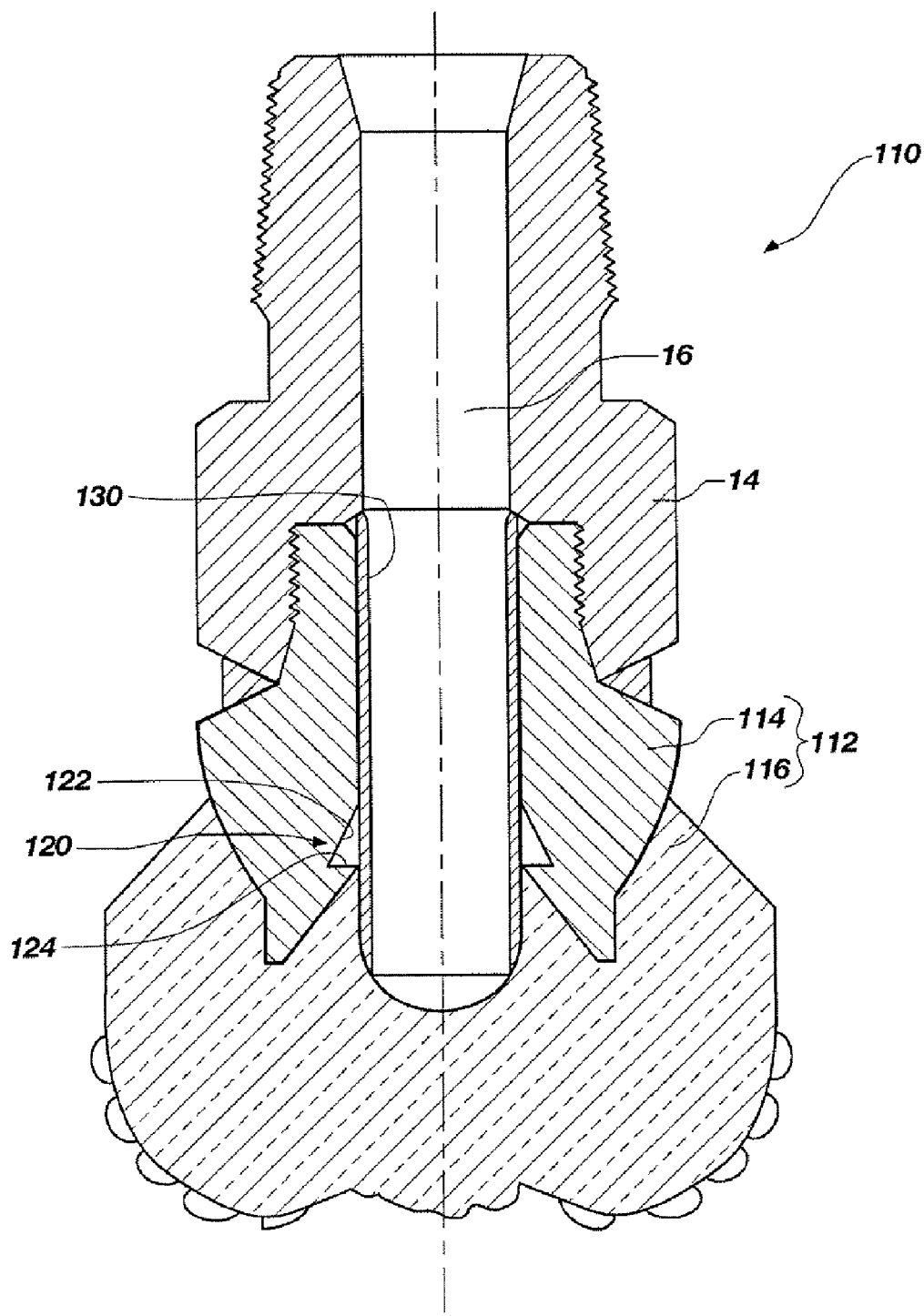
FIG. 7 is a cross-sectional view of another embodiment of a matrix-type drill bit according to the present invention and that is configured to facilitate nondestructive ultrasonic evaluation thereof.

A matrix-type drill bit 110 according to an embodiment of the present invention and includes a landing pad for an ultrasonic transducer is shown in FIG. 7. The drill bit 110 is similar to the drill bit 100 shown in FIG. 6 and includes a lower bit body 112 and an upper shank 14. A longitudinally extending bore 16 is provided through the drill bit 110. The bit body 112 includes a steel blank 114 and a bit body matrix 116. In contrast to the drill bit 100 shown in FIG. 6, however, the steel blank 114 of the drill bit 110 shown in FIG. 7 includes a landing pad cavity 120 for an ultrasonic probe. The landing pad cavity 120 may be configured as a circumferential notch formed in the inner surface of the steel blank 114 within the bore 16 of the drill bit. The landing pad cavity 120 may include a frustoconical, tapered upper surface 122 and a ledge or landing pad surface 124 oriented perpendicular to bore 16. An ultrasonic probe (not shown) used to inspect the drill bit 110 may include spring members configured to engage the inner surface of the drill bit 10 when the ultrasonic probe is inserted into the bore 16. As the ultrasonic probe is advanced longitudinally into the bore 16, the spring members may engage the circumferential notch of the landing pad cavity 120 and may abut against the ledge or landing pad surface 124. The ledge or landing pad surface 124 may prevent the ultrasonic probe from advancing longitudinally further into the bore 16 of the drill bit. The tapered upper surface 122 of the landing pad cavity 120 may allow the spring members to slide out of the circumferential notch of the landing pad cavity 120 and, thus, may allow the ultrasonic probe to be withdrawn from the bore 16 of the drill bit 10. In this configuration, the landing pad cavity 120 allows the ultrasonic probe to be precisely positioned in substantially the same location within the drill bit 10 each time the drill bit 10 is to be inspected. Such a configuration provides a reference location which may allow for data acquired relative to at least two different inspections to be legitimately compared.

During drilling operations, fluids are forced through the bore 16 of the drill bit 110 to the face thereof at high pressures and velocities, which may cause abrasion and erosion of interior surfaces of the drill bit 110 within the bore 16. As the steel blank 114 typically is more susceptible to abrasion and erosion than is the bit body matrix 116, a removable protective liner 130 in the form of a tube formed from an erosion and abrasion resistant material such as tungsten carbide, silicon carbide, or other erosion and abrasion resistant material known in the art may be provided within the bore 16 during drilling operations to inhibit degradation of the steel blank 114 and the landing pad cavity 120. Alternatively, the removable, protective tube liner may be formed from a material similar to that of the bit body matrix 116 and may be sized and shaped to protect the interior surface of the steel blank 104. The removable protective tube liner 130 may be removed from the drill bit 100 when the bit body 102 is to be ultrasonically inspected and replaced prior to subsequent drilling operations. The removable protective tube liner 130 may be removably attached to the drill bit 110 by brazing, adhesive bonding, or mechanical affixation (such as, for example, by resilient elements radially engaging landing pad cavity 120) to allow removal of the protective tube 130 from the drill bit 110 when the drill bit is to be ultrasonically inspected.

A removable protective liner such as the removable protective tube liner 130 also may be used in conjunction with the drill bit 100 shown in FIG. 6 to inhibit erosion and abrasion of the steel blank 104.

In another embodiment of the invention, a landing pad cavity or other reference element may be formed in the bit body matrix 116 of the bit body 112 during formation thereof instead of machining a landing pad in the steel blank 114.

Instead of providing a landing pad cavity or other reference element to accurately position an ultrasonic probe within the bore of a drill bit, a removable positioning member may be provided for positioning the ultrasonic probe relative to the bore. The positioning member may be configured to engage at least a portion of the bottom surface of the bore, at least a portion of the side walls of the bore, or both, to position the positioning member and ultrasonic probe at substantially the same location each time the positioning member and probe are positioned within the bore. For example, the positioning member may be configured as a fixture for supporting the ultrasonic probe and engaging at least one interior surface of the drill bit within the bore thereof. An ultrasonic probe may be positioned within the fixture, and the fixture and ultrasonic probe may be positioned within the bore of the drill bit such that the fixture engages the at least one interior surface of the drill bit within the bore and the ultrasonic probe is positioned at a selected location within the bore of the drill bit.

Each of the ultrasonic inspection techniques and methods discussed herein above has included inspecting the bit body of a drill bit using an ultrasonic probe positioned within a bore of a drill bit. In alternative methods, a drill bit may be ultrasonically inspected from the exterior of the drill bit. A ring-shaped ultrasonic probe may be provided having an inner diameter greater than the outer diameter of the bit body to allow the ring-shaped ultrasonic probe to be positioned such that the probe encircles at least a portion of the exterior surface of the drill bit. The ultrasonic probe may include a plurality of individual ultrasonic transducers oriented radially inwardly and arranged about the circumference of the ultrasonic probe to provide a selected circumferential coverage of the bit body. In addition, the individual ultrasonic transducers may be provided at various angles relative to the longitudinal axis of the drill bit or be pivotably mounted with respect thereto. In yet other methods, a drill bit may be ultrasonically inspected by emitting ultrasonic waves from a first ultrasonic probe 56 positioned within the longitudinal bore of the drill bit, transmitting the ultrasonic waves through the drill bit to the exterior thereof, and detecting the ultrasonic waves using a second ultrasonic probe 56A positioned on the exterior of the drill bit, as shown in FIG. 6A. Similarly, a drill bit may be ultrasonically inspected by emitting ultrasonic waves from a first ultrasonic probe 56A positioned on the exterior of the drill bit, transmitting the ultrasonic waves through the drill bit to the interior longitudinal bore, and detecting the ultrasonic waves using a second ultrasonic probe 56 positioned within the longitudinal bore of the drill bit.

Further, it is contemplated that movable "mirrors" having surfaces of a material reflective of ultrasound may be used in conjunction with stationary ultrasonic transducers to reflect emitted ultrasonic pulses into the drill bit at desired angles. In this configuration, the ring-shaped ultrasonic probe may be used to inspect the drill bit from the exterior thereof. Inspecting a drill bit from a position exterior of the drill bit may present difficulties associated with the presence of the bore and the material interfaces between the probe and the defects that are to be inspected. It has been observed by the inventors of the present invention that these difficulties may be mitigated or overcome by performing the ultrasonic inspection from within the bore of the drill bit.

The nondestructive ultrasonic inspection techniques, methods, systems, and apparatuses disclosed herein may be used to inspect drill bits over their life spans to identify and characterize at least one defect therein. The probability that a drill bit will fail catastrophically during a drilling operation is at least partially a function of the magnitude of the loads or forces applied to the drill bit during drilling operations, the fracture properties of the materials and the overall structure of the drill bit, and the presence of defects within the drill bit. One or more defects within a drill bit may not necessarily cause catastrophic failure of the drill bit during use. The probability that one or more defects within a drill bit will cause a drill bit to fail catastrophically during use (i.e., the criticality of the defect) is at least partially a function of the number, shape, size, nature, and location of the defects within the drill bit.

It should be understood that the inspection methods and techniques described herein may be used for inspection of any part of a rotary drill bit. For example, a bit body, a shank, a weld, or any other portion of a rotary drill bit may be inspected using the methods and techniques described herein. In one specific, non-limiting example, the techniques disclosed herein may be employed for inspection of the internal integrity of circumferential, or girth weld 32 between a bit blank 26 and a shank 14 (see FIG. 1) on the exterior of a drill bit as well as its interfaces with bit blank 26 and shank 14. Furthermore, the inspection methods and techniques described herein have been described with reference to matrix-type drill bits. The inspection methods and techniques are not so limited, however, and may be applied to other types of drill bits including drill bits having steel bit bodies and drill bits having bit bodies comprising particle-matrix composite materials formed by particle compaction and densification techniques, such as those described in pending U.S. patent application Ser. No. 11/271,153, filed Nov. 10, 2005 and pending U.S. patent application Ser. No. 11/272,439, also filed Nov. 10, 2005.

Also, the inspection methods and techniques may be used to inspect drilling tools other than conventional matrix-type rotary drill bits such as, for example, core bits, casing bits, reamers, bi-center and eccentric rotary drill bits, reamer wings, steel body drill bits, roller cone drill bits, and other drilling tools as known in the art. The specific materials, sizes and internal and external configurations of any of the foregoing are nonlimiting of the utility of the present invention.

The inspection methods and techniques described hereinabove may be used to predict whether a drilling tool will fail under predetermined drilling conditions. By way of example and not limitation, the inspection methods and techniques described hereinabove may be used to identify and characterize one or more cracks or other defects in an earth-boring rotary drill bit 10 like that shown in FIG. 1. If the materials from which the earth-boring rotary drill bit 10 is formed are known, the properties of the materials (e.g., the fracture toughness $K_c$ and the critical stress for crack propagation $\sigma_c$ for crack propagation) may be determined using conventional standard test methods known in the art (e.g., ASTM (American Society for Testing and Materials) Standard Test Method E 1820-98, which is entitled Measurement of Fracture Toughness). A computational model of the drill bit 10 that includes the identified and characterized cracks or defects therein may be generated. Finite element analysis (FEA) techniques then may be used to calculate estimated stress intensity factors K and effective stresses σ that may be generated in the drill bit 10 due to anticipated forces (e.g., weight-on-bit (WOB) and torque) that may be applied to the drill bit 10 during a subsequent drilling operation. Equations for calculating stress intensity factors K and effective stresses σ, as well as fracture toughness KC and fracture stress for crack propagation $\sigma_f$, are known in the art and described at, for example, Pages 31-96 of T. L. Anderson, Fracture Mechanics: Fundamentals and Applications, CRC Press, Inc., (2nd edition, 1995), the contents of which are incorporated herein in their entirety by this reference. Once these values have been determined, a failure assessment diagram (FAD) may be generated and used to predict whether the drill bit 10 will fail under the anticipated drilling conditions. Such failure assessment diagrams are known in the art and described at, for example, Pages 459-478 of T. L. Anderson, Fracture Mechanics: Fundamentals and Applications, CRC Press, Inc., (2nd edition, 1995), the contents of which are also incorporated herein in their entirety by this reference. By way of example and not limitation, if the ratio of the effective stress σ to the critical stress for crack propagation $\sigma_f(\sigma/\sigma_f)$ is greater than or equal to about 0.8, it may be predicted that the drill bit 10 will fail due to a plastic failure mechanism. If the ratio of the stress intensity factor K to the fracture toughness $K_c(K/K_c)$ is greater than or equal to about 0.8, it may be predicted that the drill bit 10 will fail due to a brittle failure mechanism. In this manner, the methods described herein may be used to predict failure of drill bits and other drilling tools before they are actually used in a drilling operation to prevent failure of the drill bit or other drilling tool.

While the present invention has been described herein with respect to certain preferred embodiments, those of ordinary skill in the art will recognize and appreciate that it is not so limited. Rather, many additions, deletions and modifications to the preferred embodiments may be made without departing from the scope of the invention as hereinafter claimed. In addition, features from one embodiment may be combined with features of another embodiment while still being encompassed within the scope of the invention as contemplated by the inventors.

What is claimed is:

1. A method for conducting nondestructive inspection of a drill bit for subterranean drilling comprising:
    communicating ultrasonic waves into a rotary drill bit from within a longitudinal bore of the rotary drill bit using an ultrasonic system;
    detecting ultrasonic waves reflected from one or more features of the rotary drill bit from within the longitudinal bore of the rotary drill bit; and
    using the detected, reflected ultrasonic waves to calibrate at least one component of the ultrasonic system and to confirm the presence or absence of at least one defect within the rotary drill bit.

2. A method for conducting nondestructive inspection of a drill bit for subterranean drilling comprising:
    inserting at least one of an ultrasonic energy emitter and an ultrasonic energy receiver into a longitudinal bore of a rotary drill bit;
    positioning the at least one of the emitter and the receiver at a known location relative to the drill bit using at least one reference feature of the drill bit;
    communicating ultrasonic waves into at least a portion of the rotary drill bit from the ultrasonic energy emitter;
    detecting ultrasonic waves that are at least one of reflected and refracted by the at least a portion of the rotary drill bit using the ultrasonic energy receiver; and
    generating a representation of at least a portion of the rotary drill bit using the detected ultrasonic waves.

3. The method of claim 2, further comprising using a single ultrasonic probe as the emitter and the receiver.

4. The method of claim 2, further comprising positioning at least one of the emitter and the receiver at a predetermined selected location relative to the drill bit using at least one reference position feature.

5. The method of claim 2, further comprising generating a graphical representation of at least one defect within the rotary drill bit from the detected ultrasonic waves.

6. The method of claim 2, wherein communicating ultrasonic waves comprises directing the ultrasonic waves into the at least a portion of the rotary drill bit from within a longitudinal bore of the rotary drill bit, and wherein detecting ultrasonic waves comprises detecting the ultrasonic waves from within the longitudinal bore of the rotary drill bit.

7. The method of claim 2, wherein communicating ultrasonic waves comprises directing the ultrasonic waves into the at least a portion of the rotary drill bit from within a longitudinal bore of the rotary drill bit, and wherein detecting ultrasonic waves comprises detecting the ultrasonic waves from a location exterior to the drill bit.

8. The method of claim 2, communicating ultrasonic waves comprises directing the ultrasonic waves into the at least a portion of the rotary drill bit from a location exterior to the drill bit, and wherein detecting ultrasonic waves comprises detecting the ultrasonic waves from within the longitudinal bore of the rotary drill bit.

9. The method of claim 2, further comprising sonically coupling at least one of the ultrasonic energy emitter and the ultrasonic energy receiver to the rotary drill bit.

10. The method of claim 9, wherein sonically coupling comprises filling at least a portion of a longitudinal bore of the rotary drill bit with an ultrasonic couplant.

11. The method of claim 10, wherein sonically coupling comprises immersing at least a portion of the rotary drill bit in an ultrasonic couplant.

12. A method for conducting nondestructive inspection of a drill bit for subterranean drilling comprising:
    communicating ultrasonic waves into at least a portion of a rotary drill bit from an ultrasonic energy emitter;
    detecting ultrasonic waves that are at least one of reflected and refracted by the at least a portion of the rotary drill bit using an ultrasonic energy receiver; and generating a representation of at least a portion of the rotary drill bit using the detected ultrasonic waves;
    communicating the ultrasonic waves onto at least one reference calibration feature on the rotary drill bit;
    detecting ultrasonic waves that are at least one of reflected and refracted from the at least one reference calibration feature; and
    calibrating the ultrasonic probe using the detected ultrasonic waves that are at least one of reflected and refracted from the at least one reference calibration feature and at least one known dimension of the at least one reference calibration feature.

13. The method of claim 12, wherein communicating ultrasonic waves comprises directing the ultrasonic waves into the at least a portion of the rotary drill bit from a location exterior to the drill bit, and wherein detecting ultrasonic waves comprises detecting the ultrasonic waves from a location exterior to the drill bit.

14. A method for conducting nondestructive inspection of a drill bit for subterranean drilling comprising:

communicating ultrasonic waves into at least a portion of a rotary drill bit from an ultrasonic energy emitter;

detecting ultrasonic waves that are at least one of reflected and refracted by the at least a portion of the rotary drill bit using an ultrasonic energy receiver; and generating a representation of at least a portion of the rotary drill bit using the detected ultrasonic waves; and positioning at least one of the emitter and the receiver at a predetermined selected location relative to the drill bit using at least one landing pad formed in a surface of the drill bit.

\* \* \* \* \*

UNITED STATES PATENT AND TRADEMARK OFFICE
CERTIFICATE OF CORRECTION

PATENT NO. : 7,631,560 B2  
APPLICATION NO. : 11/787693  
DATED : December 15, 2009  
INVENTOR(S) : Jeffrey B. Lund et al.

It is certified that error appears in the above-identified patent and that said Letters Patent is hereby corrected as shown below:

In the specification:

| | | |
|---|---|---|
| COLUMN 6, | LINE 8, | change "movable" to --cantilevered support-- |
| COLUMN 6, | LINE 26, | change "movable" to --cantilevered support-- |
| COLUMN 9, | LINE 40, | change "member" to --member 64-- |
| COLUMN 10, | LINE 11, | change "probe" to --probe 56-- |
| COLUMN 11, | LINES 36, 37, | change "disc shaped" to --disc-shaped-- |
| COLUMN 11, | LINE 39, | change "disc shaped" to --disc-shaped-- |
| COLUMN 11, | LINE 41, | change "disc shaped" to --disc-shaped-- |
| COLUMN 14, | LINE 27, | change "drill bit." to --drill bit 110.-- |
| COLUMN 14, | LINE 32, | change "drill bit 10" to --drill bit 110-- |
| COLUMN 14, | LINE 43, | change "drill bit 10." to --drill bit 110.-- |
| COLUMN 14, | LINE 46, | change "bit 10 each time the drill bit 10" to --bit 110 each time the drill bit 110-- |

Signed and Sealed this  
Twenty-fourth Day of January, 2012

David J. Kappos  
*Director of the United States Patent and Trademark Office*